(12) United States Patent
Knochel et al.

(10) Patent No.: US 6,184,404 B1
(45) Date of Patent: Feb. 6, 2001

(54) PROCESS FOR THE SELECTIVE ALKYLATION OF ALDEHYDES BY MEANS OF ORGANOZINC COMPOUNDS

(75) Inventors: Paul Knochel, Marburg; Christian Lutz, Weil am Rhein, both of (DE)

(73) Assignee: Metallgesellschaft Aktiengesellschaft, Frankfurt am Main (DE)

( * ) Notice: Under 35 U.S.C. 154(b), the term of this patent shall be extended for 0 days.

(21) Appl. No.: 09/258,927

(22) Filed: Mar. 1, 1999

(30) Foreign Application Priority Data

Mar. 5, 1998 (DE) .............................. 198 09 341

(51) Int. Cl.⁷ .............................. C07F 3/06; C07C 45/00
(52) U.S. Cl. .................. 556/121; 556/129; 556/118; 568/433; 568/458
(58) Field of Search ..................... 568/433, 458; 528/86; 556/118, 121, 129

(56) References Cited

PUBLICATIONS

Bertz et al; Journal of American Chemical Society, 118, pp. 10906–10907, 1996.*

Lutgens et al, Organometallics, 16, pp. 5869–5878, 1997.*

Knochel et al; Journal of Organic Chemistry, 62, pp. 7895–7898, 1997.*

* cited by examiner

*Primary Examiner*—Sreeni Padmanabhan
(74) *Attorney, Agent, or Firm*—Fulbright & Jaworski, LLP

(57) ABSTRACT

There is described a process for the enantioselective alkylation of aldehydes by means of organozinc compounds, of which a ligand of the zinc is transferred to the aldehyde, and the other ligand acts as so-called dummy ligand. As novel substances there are used zinc-organic compounds, which contain the neophyl residue as dummy ligand.

12 Claims, No Drawings

PROCESS FOR THE SELECTIVE ALKYLATION OF ALDEHYDES BY MEANS OF ORGANOZINC COMPOUNDS

This invention relates to a process for the selective alkylation of aldehydes by means of organozinc compounds.

Organozinc compounds R—Zn—X or $R_2Zn$ (R=alkyl, aryl, x=Cl, Br, I) are easy-to-handle organometallic reagents, which in the synthesis can be used for selective CC cross-linking reactions, where due to the low reactivity of the zinc species the transfer of the residue R requires the presence of a further transition metal compound, e.g. a copper, palladium, cobalt or titanium compound. A particular advantage of the zinc-organic chemistry consists in the fact that the above-mentioned organic residues R can also have a functional group FG, such as an ester, amine or nitrile function. (A good survey is provided by P. Knochel and R. D. Singer in Chem. Rev. 1993, 93, 2117–2188).

Of particular importance is the transfer of functionalized organic residues (R-FG) to aldehydes, as this reaction takes place enantioselectively in the presence of suitable chiral auxiliaries (ligands):

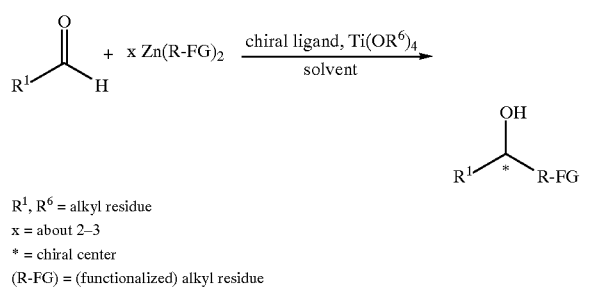

$R^1$, $R^6$ = alkyl residue
x = about 2–3
* = chiral center
(R-FG) = (functionalized) alkyl residue In this way, functionalized secondary alcohols can in general be produced with good yields and very good enantiomeric purities (>90%). This excellent selectivity is paid for with a relatively poor reactivity of the Zn species. The latter leads to the fact that the zinc compound must generally be used with a two- or threefold excess, i.e. from the amounts (R-FG) used only about 15 to 30% are transferred to the aldehyde in the final analysis. The rest is lost during processing. The same is true for the titanium compound used as co-reagent, which must preferably be used in about equimolar amounts (based on the Zn compound).

To increase the utilization of the zinc-bound alkyl residue, there were used recently mixed zinc compounds of the type

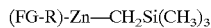

[C. Lutz, P. Knochel, J. Org. Chem. 1997, 62, 7895]. It was found that the $H_2C$—$Si(CH_3)_3$ residue ("TMSM") is not transferred to carbonyl compounds and thus a desired chemoselective transfer of the functionalized alkyl residue (R-FG) is ensured.

In this way, the residue (R-FG) to be transferred is required in considerably lower amounts. This is of high interest in particular for valuable functionalized residues. For technical applications, the TMSM residue is, however, less suited because of a lack of availability and because of the high price of its precursor compound Cl—$CH_2$—Si $(CH_3)_3$.

It is therefore the object underlying the invention to eliminate the disadvantages known from the prior art and in particular create a process for the (enantioselective) alkylation of aldehydes by means of zinc-organic compounds, wherein the alkyl residue to be transferred can be present in a functionalized form and saturates only one valency each of the zinc, and the second zinc compound is saturated by an easily accessible and in expensive residue ("dummy ligand") which does not disturb the alkylation.

It is a further object of the invention to create novel compounds, by means of which the (enantioselective) alkylation of aldehydes can be performed to a particular advantage corresponding to the inventive process.

Despite the prejudice described in the literature [Steven H. Bertz et al., J. Am. Chem. Soc. 1996, 118, 10906], which postulates that for stabilizing the Zn dummy bond (and thus the non-transfer of the dummy ligand) an Si atom in β-position with respect to the Zn atom (β-silyl effect with respect to metal centers) is required as in the case of the above-mentioned TMSM residue, it was surprisingly found out that also a number of simple, silicon-free, organic residues of the type

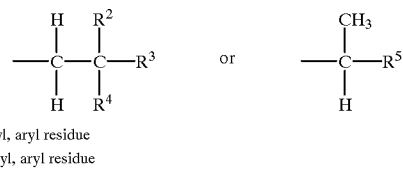

$R^2$ = H, alkyl, aryl residue
$R^3$, $R^4$ = alkyl, aryl residue
$R^5$ = alkyl residue are likewise able to act as dummy ligands in the above-described zinc-organic compounds. There are preferably used alkyl residues with 1 to 8 C atoms and phenyl residues which can optionally carry in addition one or more alkyl substituents, in particular dummy ligands with $R^2$=phenyl and $R^3$, $R^4$=methyl, or with $R^2$, $R^3$, $R^4$=methyl. The essential features of the inventive process are stated in claim 1. Sub-claims 2 to 10 disclose features which develop the inventive process. Claims 11 and 12 refer to a new group of dialkylzinc compounds by means of which the chemoselective transfer of (functionalized) alkyl residues in accordance with the inventive process takes place particularly easily.

For performing the inventive process basically all aldehydes and in particular the following aldehydes may be used: saturated aldehydes with n-alkyl chains and branched alkyl chains, aromatic and heteroaromatic aldehydes, benzaldehyde, substituted benzaldehyde, such as anisaldehyde, pyridine-2-carbaldehyde, pyridine-3-carbaldehyde, pyridine-4-carbaldehyde, quinoline-3-carbaldehyde, quinoline-4-carbaldehyde, isoquinoline-4-carbaldehyde and further heteroaromatic aldehydes, unsaturated aldehydes, cinnamic aldehyde and derivatives, alkenals, 1-cyclopentene-1-carbaldehyde, 1-cyclohexene-1-carbaldehyde, alkinals, functionalized aldehydes, aminoaldehydes and hydroxyaldehydes.

As a reaction for the (enantioselective) alkylation of aldehydes by means of such zinc-organic compounds, whose one ligand consists of the (functionalized) residue (R-FG) to be transferred chemoselectively, and whose other ligand consists of an easily accessible and inexpensive dummy, the following reaction was chosen:

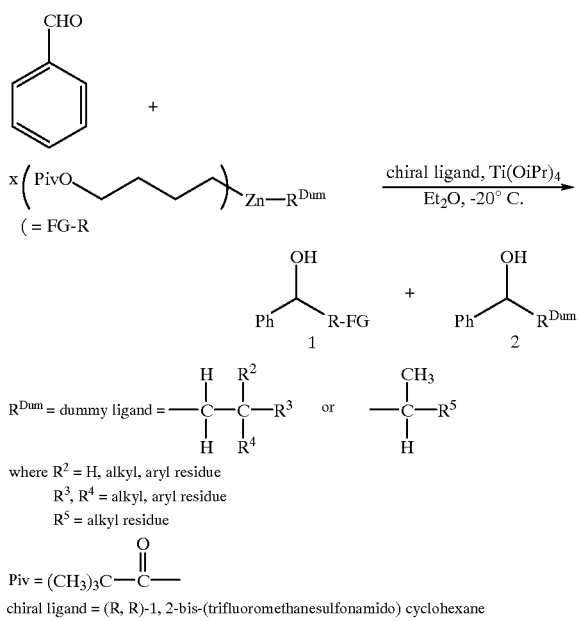

| | | x | Yield isolated | 1:2[1] | ee1[2] |
|---|---|---|---|---|---|
| $R^2, R^3, R^4 = Me$ | (neopentyl) | 2.4 | 82% | 100:0 | 89% |
| $R^2, R^3 = Me,$ $R^4 = Ph$ | (neophyl) | 2.4 | 82% | 100:0 | 89% |
| $R^2, R^3 = Me,$ $R^4 = H$ | (i-Bu) | 2.4 | — | 95:5 | 94% |
| $R^5 = Me$ | (i-Pr) | 2.4 | — | 82:18 | rac. |

[1] Determined by a) GC column and b) HPLC analysis; a) Chrompack Chirasil CB, carrier gas $H_2$, 100 kPa; b) Chiracel OD; UV detector, 215 nm.
[2] Determined by chiral HPLC analysis, Chiracel OD.
ee = percentage excess of the enantiomer with respect to the racemate.

In this case, the catalyst system for the addition of mixed (partly functionalized) dialkylzinc compounds to aldehydes consists of (R,R)-1,2-bis-(trifluoromethanesulfonamido) cyclohexane as chiral ligand and titanium tetraisopropylate as Lewis acid. As can be seen from the results of the test reaction indicated in the above table, in the case of the neopentyl (dummy) ligand ($R^2, R^3, R^4 = Me$) and of the neophyl (dummy) ligand ($R^2, R^3 = Me, R^4 = Ph$) only the desired residue (R-FG), in this case 4-pivaloxybutyl, is transferred to the aldehyde, namely largely enantioselectively. A change to sterically less demanding dummy ligands, such as isobutyl ($R^2, R^3 = Me, R^4 = H$) and isopropyl ($R^5 = Me$), leads to a partial transfer of the dummy ligand to the aldehyde (5% or 18%). Nevertheless, the desired reaction product 1 is still obtained in a clear excess with respect to the undesired product 2.

Thus, it has been shown that by means of the inventive process the residue (R-FG) to be transferred is transferred chemoselectively from the dialkylzinc compound to the aldehyde, where the dummy ligand of the dialkylzinc compound consists of easily accessible and inexpensive organic residues. Furthermore, with this novel process there can in general also be achieved good enantiomeric purities.

When the residue (R-FG) to be transferred consists of simple, non-functionalized alkyl residues ($C_1$–$C_{12}$), the addition of the mixed dialkylzinc reagent can be reduced from x=2.4 to x=1.6 equivalents. In general, these dialkylzinc reagents are more reactive than dialkylzinc compounds in which (R-FG) is a functionalized alkyl residue.

For performing the inventive process, 1 to 40 mol-%, preferably 2 to 20 mol-% (based on the aldehyde) of a chiral ligand (e.g. (R,R)-1,2-bis-(trifluoromethanesulfonamido) cyclohexane or (S,S)-1,2-bis-(trifluoromethanesulfonamido)cyclohexane) in a solvent such as a hydrocarbon ($C_5$–$C_{12}$), an aromatic hydrocarbon (preferably toluene), an ether (preferably diethyl ether) or a chlorinated hydrocarbon (preferably dichloromethane) are suspended or dissolved at room temperature. Subsequently, 0.1 to 2.0 equivalents, preferably 0.6 to 1.2 equivalents (based on the aldehyde) Lewis acid, e.g. titanium or zirconium tetraalkoxide, preferably titanium tetraisopropylate, are added.

This catalyst solution is now cooled (about −20° C. to 0° C.) and mixed with 1.0 to 3.0 equivalents, preferably 1.6 to 2.4 equivalents (based on the aldehyde) of the mixed (possibly functionalized) dialkylzinc compound. There is obtained a yellow solution, which is tempered to the desired reaction temperature by means of a cryostat. The addition reactions can be performed at a temperature in the range from −80° C. to −50° C., preferably at −20° C. To catalyst and reagent, 1 equivalent aldehyde is added slowly. As aldehyde, there may be used aldehydes carrying aromatic, heteroaromatic, aliphatic, unsaturated and functional groups. Functional groups (FG) may be: ester, amine and nitrile functions.

Upon completion of the reaction, processing is performed corresponding to the physicochemical properties of the products. Frequently, there is first of all performed a hydrolysis with saturated $NH_4Cl$ solution, and the precipitate obtained is dissolved with little 10% aqueous hydrochloric acid. Alternatively, the organic phase is hydrolyzed with organic acids and/or water. Upon separation of the organic phase and repeated extraction of the aqueous phase, the combined organic phases are washed for instance with 2N sodium hydroxide solution and dried by means of drying agents such as magnesium sulfate or sodium sulfate. By acidifying the aqueous, basic phase with dilute sulfuric acid (pH-value about 2), the chiral ligand (R,R)-1,2-bis-(trifluoromethanesulfonamido)cyclohexane can be extracted with diethyl ether and be reused.

Mixed dialkylzinc compounds are known in principle. As these compounds are most favorably produced from commercially available diethylzinc, these are chiefly ethyl zinc alkyls.

As a new group of dialkylzinc compounds, with which the chemoselective transfer of (functionalized) alkyl residues is effected particularly easily according to the inventive process, there were found dialkylzinc compounds which include the neophyl residue as dummy ligand. These compounds are not known so far.

For producing the mixed dialkylzinc reagents three methods are available:

1. Transfer of the dummy ligand by means of the corresponding alkyllithium or alkyl magnesium halogen or dialkyl magnesium compound to the functionalized alkyl zinc halide (transmetallation).

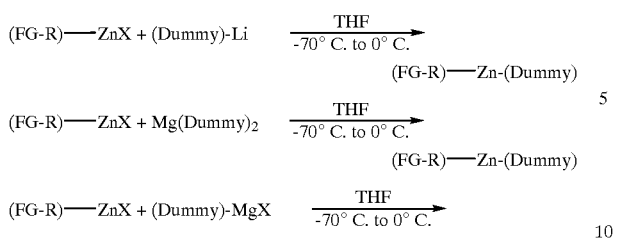

$X = (Cl), Br, I$

Alkyl zinc halides can easily be prepared from zinc and alkyl halide by zinc insertion into the corresponding carbon-halogen bond. What should be noted here is the high tolerance with respect to other functional groups in the alkyl residue, such as ester, amine or nitrile functions.

2. Transfer of the (functionalized) alkyllithium or alkyl magnesium halogen compound or dialkyl magnesium compound to the alkyl zinc halide of the dummy ligand (transmetallation reversed with respect to 1.).

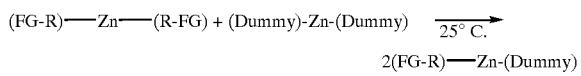

$M = Li, Mg, MgX$
$X = (Cl), Br, I$

3. Mixing the two dialkylzinc reagents (functionalized dialkylzinc compound and dummy dialkylzinc compound) to obtain the mixed dialkylzinc compound.

(FG-R)—Zn—(R-FG) + (Dummy)-Zn-(Dummy) $\xrightarrow{25°C.}$

2(FG-R)—Zn-(Dummy)

The dialkylzinc compounds can be obtained according to methods known from the literature. For the synthesis of functionalized dialkylzinc reagents there may be used in particular the iodine-zinc exchange known per se or the boron-zinc exchange known per se.

Method 3. is particularly important, as here no salts are formed as byproducts. The presence of salts can negatively influence the above-described enantioselective addition of the (functionalized) alkyl residue (R-FG) to aldehydes (low conversion, poor enantioselectivity).

The process described above can also be performed with further catalyst systems (consisting of a chiral ligand and possibly a Lewis acid). As is known, there are generally two classes of catalyst systems: 1. chirally modified Lewis acids, and 2. chiral amino alcohols.

The following further catalysts were tested:
1. Chirally modified Lewis acids:

VII

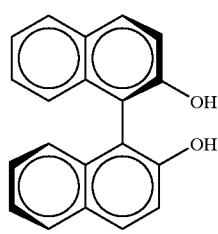

IX

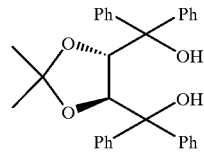

(and the respective other enantiomer)

2. Amino alcohols:

XI

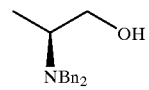

$Bn = benzyl$

XIII

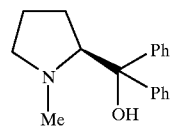

(and the respective other enantiomer)

As reaction there was chosen the addition of the ethyl residue to benzaldehyde by using the neopentyl residue as dummy ligand:

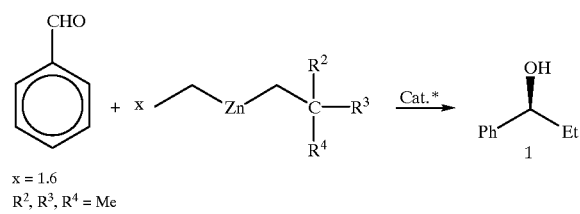

$x = 1.6$
$R^2, R^3, R^4 = Me$

| Cat. * | X | Yield isolated | ee1[1] |
|---|---|---|---|---|
| $R^2,R^3,R^4 = Me$ (neopentyl) | 2 mol-% VII + Ti(OiPr)$_4$, diethyl ether, −20° C. | 1.6 | 92% | 86% |
| $R^2,R^3,R^4 = Me$ (neopentyl) | 10 mol-% IX + Ti(OiPr)$_4$, diethyl ether −20° C. | 1.6 | 87% | 79% |
| $R^2,R^3,R^4 = Me$ (neopentyl) | 10 mol-% XI, toluene RT | 1.6 | 81% | 65% |
| $R^2,R^3,R^4 = Me$ (neopentyl) | 2 mol-% XIII, toluene RT | 1.6 | 74% | 82% |

[1]Determined by chiral HPLC analysis, Chiracel OD.
Data in mol-%, based on aldehyde.

The results of the test reaction indicate that chirally modified Lewis acids or chiral amino alcohols can be used as chiral ligands (catalysts) in the process in accordance with the invention.

As compared to the previously known methods, the process in accordance with the invention allows to selectively and thus economically transfer only the (functionalized) residue (R-FG) of a dialkylzinc compound to aldehydes, i.e. instead of previously only about 15 to 30% of the used amount (R-FG), about 30 to 50% can now be transferred. Advantageously, high enantiomeric purities can be achieved, in particular when using the inventive dialkylzinc compounds with the neophyl residue as dummy ligand. In the case of dummy ligands, commercially available, inexpensive raw materials may be used. Furthermore, the amount of Lewis acid (co-catalyst) to be added can be reduced from previously 2 to 3 equivalents to preferably about 0.6 to 1.2 equivalents, and other catalyst systems may also be used.

EMBODIMENTS

Examples 1 and 2 refer to the synthesis of (S)-5-hydroxy-5-phenylpentylpivalate by means of the inventive process; in Example 1 the neophyl residue was used as dummy ligand, and in Example 2 the neopentyl residue was used as dummy ligand.

Examples 3 to 5 describe the synthesis of (S)-1-phenylethanol, where Example 3 was performed in accordance with the prior art, and for comparison purposes, the inventive process was employed in Examples 4 and 5.

EXAMPLE 1

Synthesis of (S)-5-hydroxy-5-phenylpentylpivalate by enantioselective addition of the 4-pivaloxybutyl group to benzaldehyde by using the corresponding neophyl zinc compound and preparation of the neophyl zinc compound Preparation of neophyl zinc iodide:

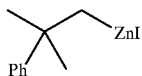

In a round flask including nitrogen preparation, internal thermometer and septum cap, which was heated in a vacuum and rinsed with argon, zinc powder (1.57 g, 24.0 mmol) was covered with a layer of THF (6 ml) and presented, and 1,2-dibromomethane (0.2 ml) was slowly added dropwise from a single-use syringe with cannula. Upon addition, heating was effected by means of a hot-air blast until the solvent was slightly boiling. After the reaction mixture was cooled to room temperature, trimethylsilylchloride (0.2 ml) was slowly added dropwise. By means of a hot-air blast, the mixture was again heated until it was slightly boiling, and stirring was continued for 5 minutes. Subsequently, 1-(2-iodo-1,1-dimethylethyl)benzene (neophyl iodide, 1.56 g, 6.0 mmol) was added within 5 minutes. Upon completion of the addition, the mixture was heated to 50° C. for 3 hours. The zinc insertion was observed by means of a GC analysis via iodolysis and hydrolysis of an aliquot of the reaction mixture.

Preparation of dineophyl zinc:

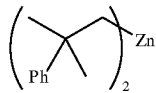

In a heated 250 ml three-necked round flask including reflux cooler, drip funnel and nitrogen cock, which was rinsed with argon, magnesium (4.0 g, 165 mmol) was covered with a layer of diethyl ether (25 ml) and activated with a few grains of iodine. 1-(2-chloro-1,1-dimethyl) benzene (neophyl chloride, 25.29 g, 150 mmol), dissolved in diethyl ether (100 ml), was slowly added dropwise. During the addition, the reaction mixture was heated until it was slightly boiling and upon completion of the addition was refluxed for another 1.5 hours. In a further round flask with nitrogen preparation, zinc bromide (16.9 g, 75 mmol) was dried in a vacuum (0.1 Torr) for 2 hours at 140° C. and dissolved in diethyl ether (100 ml) by cooling it in an ice bath. The zinc bromide solution was cooled to 0° C., and the neophyl magnesium chloride solution was slowly added by means of a transfer needle. Heating was effected to room temperature, and stirring was continued for 14 hours. The precipitated salts ($MgHal_2$) were separated by filtration through a dry reversing frit rinsed with argon (pore size D3), and the residue was washed with diethyl ether (two times 40 ml). Subsequently, the solvent was distilled off and the residue obtained was transferred by means of a transfer needle into a 100 ml round flask with nitrogen preparation. For removing solvent residues, drying was effected in a vacuum (0.1 Torr) for 1 hour. The raw product was purified by recondensation via an ether bridge in a vacuum ($1.7 \cdot 10^{-4}$ mbar) at about 150° C. (hot-air blast). The product dineophyl zinc was isolated in a 61% yield (14.6 g, 45.9 mmol).

Synthesis of the functionalized dialkylzinc reagent 4-pivaloxybutyl-neophylzinc

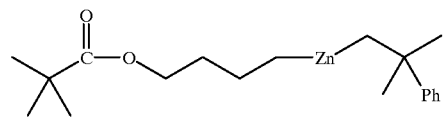

In a nitrogen flask, bis-(4-pivaloxybutyl)zinc, which proceeding from 4-iodobutylpivalate (1.56 g, 5.5 mmol) was obtained from the iodine-zinc exchange reaction in a 89% yield (which corresponds to 1.22 equivalents based on the aldehyde), was dissolved in 2 ml diethyl ether. To this solution, dineophyl zinc (0.82 g, 2.5 mmol, 1.25 equivalents) was added at room temperature.

Enantioselective addition of 4-pivaloxybutyl-neophylzinc to benzaldehyde, synthesis of (S)-5-hydroxy-5-phenylpentylpivalate

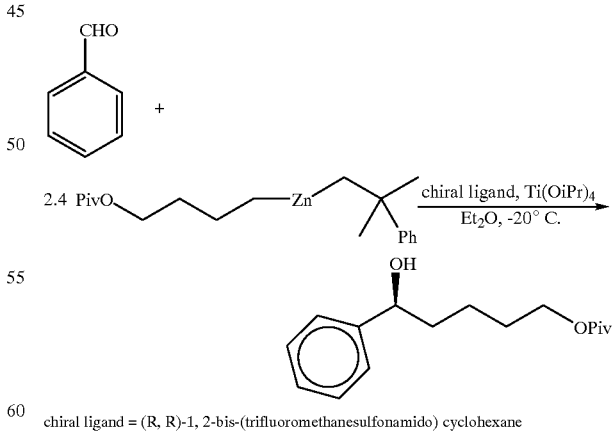

chiral ligand = (R, R)-1, 2-bis-(trifluoromethanesulfonamido) cyclohexane

In a heated, argon-flooded round flask with nitrogen cock, (R,R)-1,2-bis(trifluoromethanesulfonamido)cyclohexane (61 mg, 0.16 mmol, 8 mol-%), titanium tetraisopropylate (0.36 ml, 1.2 mmol, 0.6 equivalents) was dissolved in 3 ml diethyl ether. The catalyst solution was cooled to −20° C. The mixed dialkylzinc reagent 4-pivaloxybutyl-neophylzinc (2.4 equivalents) was slowly added dropwise to the catalyst solution. After 10 minutes, benzaldehyde (0.21 g, 2.0 mmol, 1 equivalent) was dropped in undiluted. The reaction mixture was stirred for 23 hours at −20° C. Upon hydrolysis with 20 ml saturated ammonium chloride solution and 5 ml 10% aqueous hydrochloric acid solution the organic phase was separated, and the aqueous phase was extracted three times with 50 ml diethyl ether each. The combined organic phases were washed with 2N sodium hydroxide solution and dried over magnesium sulfate. Upon removal of the solvent by distillation, the raw product was purified by means of column chromatography. The product (S)-5-hydroxy-5-phenylpentylpivalate was isolated in a yield of 82% and an enantiomeric purity of 89%. The enantiomeric purity was determined by chiral HPLC analysis, Chiracel OD, heptane/isopropanol=95:5, flow rate 0.6 ml/min; 23.95 min. main isomer, 26.41 min. secondary isomer;

$[\alpha]_D^{25} = -21.9°$ (c=2.91, CHCl$_3$).

EXAMPLE 2

Synthesis of (S)-5-hydroxy-5-phenylpentylpivalate by enantioselective addition of the 4-pivaloxybutyl group to benzaldehyde by using the corresponding neopentyl zinc compound Synthesis of the functionalized dialkylzinc reagent 4-pivaloxybutyl-neopentylzinc

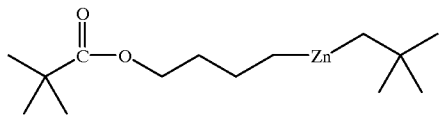

In a shaking flask bis-(4-pivaloxybutyl)zinc, which proceeding from 4-iodobutylpivalate (1.56 g, 5.5 mmol) was obtained from the iodine-zinc exchange reaction in a 89% yield (which corresponds to 1.22 equivalents, based on the aldehyde), was dissolved in 2 ml diethyl ether. Dineopentyl zinc (0.51 g, 2.5 mmol, 1.25 equivalents), which had been prepared from the corresponding Grignard compound, was added to this solution at room temperature.

Enantioselective addition of 4-pivaloxybutyl-neopentylzinc to benzaldehyde, synthesis of (S)-5-hydroxy-5-phenylpentylpivalate In a heated, argon-flooded round flask with nitrogen cock, (R,R)-1,2-bis(trifluoromethanesulfonamido)cyclohexane (61 mg, 0.16 mmol, 8 mol-%), titanium tetraisopropylate (0.36 ml, 1.2 mmol, 0.6 equivalents) was dissolved in 3 ml diethyl ether. The catalyst solution was cooled to −20° C. The mixed dialkylzinc reagent 4-pivaloxybutyl-neopentylzinc (2.4 equivalents) was slowly added dropwise to the catalyst solution. After 10 minutes, benzaldehyde (0.21 g, 2.0 mmol, 1 equivalent) was dropped in undiluted. The reaction mixture was stirred for 23 hours at −20° C. Upon hydrolysis with 20 ml saturated ammonium chloride solution and 5 ml 10% aqueous hydrochloric acid solution, the organic phase was separated and the aqueous phase was extracted three times with 50 ml diethyl ether each. The combined organic phases were washed with 2N sodium hydroxide solution and dried over magnesium sulfate. Upon removal of the solvent by distillation, the raw product was purified by column chromatography. The product (S)-5-hydroxy-5-phenylpentylpivalate was isolated in a yield of 82% and an enantiomeric purity of 89%. The enantiomeric purity was determined by chiral HPLC analysis, Chiracel OD, heptane/isopropanol=95:5, flow rate 0.6 ml/min; 23.95 min. main isomer, 26.41 min. secondary isomer;

$[\alpha]_D^{25} = -22.9°$ (c=4.19, CHCl$_3$).

From Examples 1 and 2 it can be seen that with this reaction, the neophyl and neopentyl dummy ligands lead to identical yields.

EXAMPLE 3

Synthesis of (S)-1-phenylethanol by addition of the methyl group to benzaldehyde with dimethylzinc In a shaking vessel with nitrogen preparation, which was heated in a vacuum and rinsed with argon, (R,R)-1,2-bis(trifluoromethanesulfonamido)cyclohexane (76 mg, 0.19 mmol, 8 mol-%), titanium tetraisopropylate (0.9 ml, 3.0 mmol, 1.2 equivalents) were dissolved in 3 ml diethyl ether and cooled to −20° C. Dimethylzinc (0.24 ml, 3.5 mmol) was added slowly to the catalyst solution, and stirring was continued for 20 minutes. Subsequently, benzaldehyde (0.280 g, 2.63 mmol) was slowly added dropwise. After 16 hours, hydrolysis was performed with saturated NH$_4$Cl solution, the precipitate was dissolved with 10% HCl solution and extracted with diethyl ether (three times 50 ml). Upon purification by means of chromatography (petroleum ether/Et$_2$O 4:1) the product was obtained as a clear oil in a yield of 89% (286 mg, 2.34 mmol). The GC analysis with chiral column Daicel Chirasil CD, 120° C., 100 kPa H$_2$ provided an enantiomeric purity of 23% ee (S-enantiomer 4.32 min, R-enantiomer 4.75 min).

EXAMPLE 4

Synthesis of (S)-1-phenylethanol by addition of the methyl group to benzaldehyde with methyl (neophyl)zinc In a shaking vessel with nitrogen preparation, which was heated in a vacuum and rinsed with argon, dimethylzinc (0.15 g, 1.6 mmol) was reacted with dineophylzinc (0.59 g, 1.8 mmol) at room temperature (RT) to obtain the mixed zinc compound. At the same time, (R,R)-1,2-bis(trifluoromethanesulfonamido)cyclohexane (61 mg, 0.16 mmol, 8 mol-%), titanium tetraisopropylate (0.36 ml, 1.2 mmol, 0.6 equivalents) was dissolved in 3 ml diethyl ether and cooled to −20° C. in a further shaking vessel with nitrogen preparation, which was heated in a vacuum and rinsed with argon. By means of an argon-rinsed syringe with a 20 cm cannula, methyl(neophyl)zinc was dropped into the catalyst solution, and stirring was continued for 20 min. Subsequently, benzaldehyde (287 mg, 2.7 mmol) was slowly dropped into the reaction solution. Stirring was continued for 16 hours at −20° C. Upon hydrolysis of the reaction mixture with saturated NH$_4$Cl solution, dissolving the precipitate with 10% HCl solution, and extraction with diethyl ether (three times 50 ml), the raw product obtained was purified by means of chromatography (petroleum ether/Et$_2$O 4:1). The product was obtained as a clear oil in a yield of 76% (250 mg, 2.04 mmol). The GC analysis with chiral column Daicel Chirasil CD, 120° C., 100 kPa H$_2$ provided an enantiomeric purity of 94% ee.

$[\alpha]_D^{25} = -39.20°$ (c=2.32, CHCl$_3$).

EXAMPLE 5

Synthesis of (S)-1-phenylethanol by addition of the methyl group to benzaldehyde with methyl (neopentyl)zinc In a shaking vessel with nitrogen preparation, which was heated in a vacuum and rinsed with argon, dimethylzinc (0.15 g, 1.6 mmol) was reacted with dineopentylzinc (0.37 g, 1.8 mmol) at room temperature to obtain the mixed zinc compound. At the same time, (R,R)-1,2-bis(trifluoromethanesulfonamido)cyclohexane (61 mg, 0.16 mmol, 8 mol-%), titanium tetraisopropylate (0.36 ml, 1.2 mmol, 0.6 equivalents) was dissolved in 3 ml diethyl ether and cooled to −20° C. in a further shaking vessel with nitrogen preparation, which was heated in a vacuum and rinsed with argon. Methyl(neopentyl)zinc was dropped into the catalyst solution by means of an argon-rinsed syringe with 20 cm cannula, and stirring was continued for 20 min. Subsequently, benzaldehyde (217 mg, 2.04 mmol) was slowly dropped into the reaction solution. Stirring was continued for 16 hours at −20° C. Upon hydrolysis of the reaction mixture with saturated $NH_4Cl$ solution, dissolving the precipitate with 10% HCl solution and extraction with diethyl ether (three times 50 ml), the raw product obtained was purified by means of chromatography (petroleum ether/ $Et_2O$ 4:1). The product was obtained as a clear oil in a yield of 92% (229 mg, 1.87 mmol). The GC analysis with chiral column Daicel Chirasil CD, 120° C., 100 kPA $H_2$ provided an enantiomeric purity of 93% ee.

$[\alpha]_D^{25} = -39.32°$ (c=4.92 $CHCl_3$).

The comparison of examples 3 to 5 clearly illustrates that the enantiomeric purity of 23% ee (with a substance yield of 89%) can be increased in the prior art process without dummy ligand (example 3) to 94% ee (with a substance yield of 76%) when using the neophyl residue as dummy ligand (example 4), and to 93% ee (with a substance yield of 92%) when using the neopentyl residue as dummy ligand (example 5).

It is claimed:

1. A process for the enantioselective alkylation of aldehydes with organozinc compounds, comprising transferring a functionalized alkyl group (R-FG) to an aldehyde according to the equation I

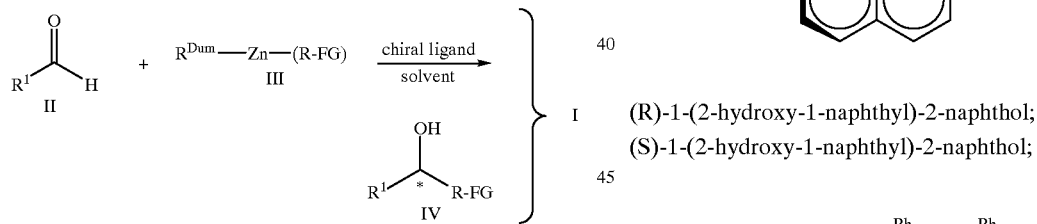

wherein $R^1$ is selected from the group consisting of alkyl, aryl, functionalized alkyl and functionalized aryl, $R^{Dum}$ is an organic residue selected from the group consisting of
—$CH_2$—$C(R^2, R^3, R^4)$ wherein
$R^2$ is selected from the group consisting of H, alkyl and aryl;
$R^3$ is selected from the group consisting of alkyl and aryl;
$R^4$ is selected from the group consisting of alkyl and aryl,
and —CH—($CH_3$)($R^5$) wherein
$R^5$ is alkyl;
(R-FG) is selected from the group consisting of alkyl and a functionalized alkyl group having a ketocarbonyl, ester, amine, carboxylic acid amide, nitrile, cyanate, isocyanate, ether, enolether, halogen, aromatic or CC multiple-bond function, wherein $R^{Dum} \neq R$-FG; and wherein the solvent is selected from the group consisting of a 5 to 12 carbon aliphatic hydrocarbon, an aromatic hydrocarbon, an ether and a chlorinated hydrocarbon, and wherein * in compound IV is a chiral center of compound IV.

2. The process of claim 1, wherein zinc compound III is added in 1.0 to 3.0 equivalents based on the aldehyde II.

3. The process of claim 2, wherein zinc compound III is added in 1.6 to 2.4 equivalents based on the aldehyde II.

4. The process of claim 1, wherein $R^{Dum}$ is selected from the group consisting of neophyl and neopentyl.

5. The process of claim 1, wherein (R-FG) of zinc compound III is an alkyl group.

6. The process of claim 1, wherein (R-FG of zinc compound III is a functionalized alkyl group having an ester, amine or nitrile.

7. The process of claim 1, wherein the chiral ligand in equation I is selected from the group consisting of (R,R)-1,2-bis-(trifluoromethanesulfonamido)cyclohexane;
(S,S)-1,2-bis-(trifluoromethanesulfonamido)cyclohexane;

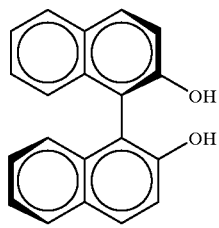

VII (R)-1-(2-hydroxy-1-naphthyl)-2-naphthol;
(S)-1-(2-hydroxy-1-naphthyl)-2-naphthol;

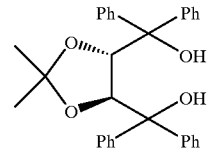

IX (4S,5S)-2,2-dimethyl-α,α,α',α'-tetraphenyl-dioxolane-4,5-dimethanol;
(4R,5R)-2,2-dimethyl-α,α,α',α'-tetraphenyl-dioxolane-4,5-dimethanol;

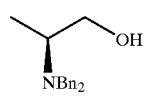

XI

Bn = benzyl (S)-2-H(dibenzylamino)propan-1-ol;
(R)-2-H(dibenzylamino)propan-1-ol;

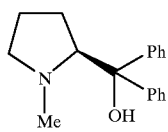

XIII (S)-diphenyl(1-methylpyrrolidin-2-yl)methanol;
(R)-diphenyl(1-methylpyrrolidin-2-yl)methanol;

and the chiral ligand is added in an amount of 0.01 to 0.4 equivalents based on the aldehyde II.

8. The process of claim 7, wherein the chiral ligand is added in an amount of 0.05 to 0.2 equivalents based on the aldehyde II.

9. The process of claim 1, further comprising adding a Lewis acid of the formula $Ti(OR^6)_4$ or $Zr(OR^6)_4$ in an amount of from 0.1 to 2.0 equivalents based on the aldehyde II wherein $R^6$ is selected from the group consisting of alkyl and aryl; and wherein the chiral ligand is selected from the group consisting of (R,R)-1,2-bis(trifluoromethanesulfonamido)cyclohexane;
(S,S)-1,2-bis(trifluoromethanesulfonamido)cyclohexane;
(R)-1-(2-hydroxy-1-naphtyl)-2-naphtol;
(S)-1-(2-hydroxy-1-naphtyl)-2-naphtol;
(4S,5S)-2,2-dimethyl-α,α,α',α'-tetraphenyl-dioxolane-4,5-dimethanol; and
(4R,SR)-2,2-dimethyl-α,α,α',α'-tetraphenyl-dioxolane-4,5-dimethanol.

10. The process of claim 9, wherein the Lewis acid is added in an amount of from 0.6 to 1.2 equivalents based on the aldehyde II.

11. The process of claim 9, wherein $R^6$ is isopropyl.

12. An alkyl-zinc compound of the formula $R^{Dum}$-Zn-(R-FG), wherein $R^{Dum}$ is neophyl and (R-FG) is selected from the group consisting of alkyl and a functionalized alkyl group having a ketocarbonyl, ester, amine, carboxylic acid amide, nitrile, cyanate, isocyanate, ether, enolether, halogen, aromatic or CC multiple-bond, and wherein (R-FG) is not neophyl.

* * * * *

UNITED STATES PATENT AND TRADEMARK OFFICE
CERTIFICATE OF CORRECTION

PATENT NO.   : 6,184,404 B1
DATED        : February 6, 2001
INVENTOR(S)  : Knochel et al.

It is certified that error appears in the above-identified patent and that said Letters Patent is hereby corrected as shown below:

Column 4,
Line 27, change "-50" to -- +50 --.

Column 11,
Line 6, claim 1, change "$(CH_3)(R_5)$" to -- $(CH_3R_5)$ --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*